United States Patent [19]

Durant et al.

[11] Patent Number: 4,649,138

[45] Date of Patent: Mar. 10, 1987

[54] PHARMACEUTICAL COMPOSITIONS

[75] Inventors: Graham J. Durant; Charon R. Ganellin; Margaret R. Vickers, all of Welwyn Garden City, England

[73] Assignee: SmithKline & French Laboratories Limited, Welwyn Garden City, England

[21] Appl. No.: 655,197

[22] Filed: Sep. 28, 1984

Related U.S. Application Data

[60] Division of Ser. No. 458,610, Jan. 17, 1983, Pat. No. 4,490,387, which is a division of Ser. No. 269,248, Jun. 1, 1981, Pat. No. 4,378,365, which is a division of Ser. No. 82,836, Oct. 9, 1979, Pat. No. 4,294,854, which is a division of Ser. No. 853,773, Nov. 21, 1977, Pat. No. 4,205,071, which is a continuation-in-part of Ser. No. 795,983, May 11, 1977, abandoned.

[51] Int. Cl.$^4$ .................. C07D 413/12; C07D 295/08; A61K 31/535

[52] U.S. Cl. .................... 514/232; 514/212; 514/218; 514/274; 514/326; 514/369; 514/578; 558/4; 540/553; 540/603; 544/139; 546/210; 548/337

[58] Field of Search ....................... 544/122, 123, 139; 260/243.3, 239 BC; 514/232, 212

[56] References Cited

U.S. PATENT DOCUMENTS

| | | | |
|---|---|---|---|
| 2,648,710 | 8/1953 | Morrison et al. ................... | 564/295 |
| 2,813,102 | 11/1957 | Winthrop ............................ | 548/351 |
| 3,334,112 | 8/1967 | Wright et al. ...................... | 548/348 |
| 3,932,644 | 1/1976 | Durant et al. ...................... | 514/341 |
| 4,152,453 | 5/1979 | Durant et al. ...................... | 514/609 |

OTHER PUBLICATIONS

Shinoda et al., "Radio Protective Activities of AET, etc.", Yakugaku Zasshi, 92(4): 442, (1972).
Ozawa et al., "Pharmacological Actions of N-Dialkyl-, etc.", Yakugaku Zasshi—88(6): 747, (1968).
Ozawa et al., "Effects of 2-Aminoethylisothiuronium (AET), etc.", Yakugaku Zasshi, 89(8): 1175, (1969).
Ozawa et al., "Inhibition of Dopamine-$\beta$-Hydroxylase, etc.," Chem. Abs. 75: 59008k, (1971).
Ozawa et al., "Effects of Guanidine, Hydrazine, etc.," Yakugaku Zasshi 90(2): 143 (1970).
Pavlova et al., "Rearrangement of Aminoalkyl-Substituted Isothiourea, etc.," Chem. Abs. 63: 1691c, (1965).
Rachinskii et al., "Rearrangements in a Series, etc.," Chem. Abs. 71: 112879r, (1969).
Hino et al., "Studies on N-Alkylated-2-(2-Aminoethyl), etc.," Chem. Pharm. Bull. 14(11): 1193, (1966).
Winthrop et al., "2-($\beta$-Dialkylaminoethylmercapto)-2-Imidazolines," Can. J. Chem. 35: 281, (1957).

*Primary Examiner*—Glennon H. Hollrah
*Assistant Examiner*—Robert Lelkes
*Attorney, Agent, or Firm*—Nancy S. Mayer; Stuart R. Suter; Alan D. Lourie

[57] ABSTRACT

S-(Aminoalkyl)isothioureas which have immunosuppressant activity. Two specific compounds are 2-(3-dimethylaminopropylthio)-2-imidazoline and N,N'-dimethyl-S-(3-dimethylaminopropyl)isothiourea.

7 Claims, No Drawings

PHARMACEUTICAL COMPOSITIONS

This is a division of application Ser. No. 458,610 filed Jan. 17, 1983 now U.S. Pat. No. 4,490,387, which is a division of application Ser. No. 269,248 filed June 1, 1981, now U.S. Pat. No. 4,378,365, which is a division of application Ser. No. 082,836 filed Oct. 9, 1979, now U.S. Pat. No. 4,294,854, which is a division of application Ser. No. 853,773 filed Nov. 21, 1977, now U.S. Pat. No. 4,205,071, which is a continuation-in-part of Ser. No. 795,983 filed May 11, 1977, now abandoned.

This invention relates to novel chemical compounds, to pharmaceutical compositions which have immunosuppressant activity and to methods of producing immunosuppressant activity.

The pharmaceutical compositions of this invention comprise a pharmaceutical carrier and, as an active constituent, an isothiourea derivative of Formula 1

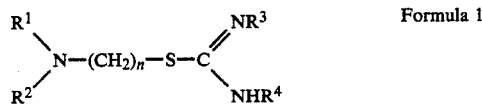

wherein n is 2, 3 or 4;

$R^1$ and $R^2$, which may be the same or different, are lower alkyl or $R^1$ and $R^2$ may together with the nitrogen atom shown form a pyrrolidine, piperidine, morpholine, 4-lower alkyl piperazine or hexahydro-1H-azepine ring, and $R^3$ and $R^4$, which may be the same or different, are lower alkyl, or together may form a $-(CH_2)_x-$ group where x is 2, 3 or 4, or a pharmaceutically acceptable acid addition salt thereof.

The compounds of Formula 1 will normally exist as acid addition salts but, for convenience, reference will be made throughout this specification to the parent compounds.

Throughout this specification by the term 'lower alkyl' we mean an alkyl group containing from 1 to 4 carbon atoms.

It is to be understood that the compounds of Formula 1 may be shown in several tautomeric forms, and pharmaceutical compositions containing any of these alternative forms are within the scope of this invention.

Particularly useful compounds are those wherein n is 2 or 3 preferably 3. Another useful group of compounds are those wherein $R^3$ and $R^4$ form a $(CH_2)_2$ group i.e., with the carbon atom and two nitrogen atoms shown they form an imidazoline ring.

Specific preferred examples of particularly active compounds of Formula 1 are pharmaceutically acceptable salts of N,N'-dimethyl-S-(3-dimethylaminopropyl)isothiourea,
N,N'-dimethyl-S-(2-dimethylaminoethyl)isothiourea,
2-(2-dimethylaminoethylthio)-2-imidazoline,
2-(3-dimethylaminopropylthio)-2-imidazoline,
2-[2-(4-morpholino)ethylthio]-2-imidazoline,
2-[2-(1-piperidino)ethylthio]-2-imidazoline and
2-[2-(1-pyrrolidino)ethylthio]-2-imidazoline.
Salts of hydrochloric acid are preferred.

We also provide novel isothiourea derivatives of Formula 1 wherein $R^1$, $R^2$, $R^3$, $R^4$, n and x have the above significance but with the proviso that when n is 2 and $R^1$ and $R^2$ are lower alkyl, $R^3$ and $R^4$ must be such that together they form a $(CH_2)_4$ group. These compounds are also objects of this invention.

The compounds of Formula 1 may be prepared according to the following scheme wherein $R^1$, $R^2$, $R^4$, $R^4$ and n have the above significance:

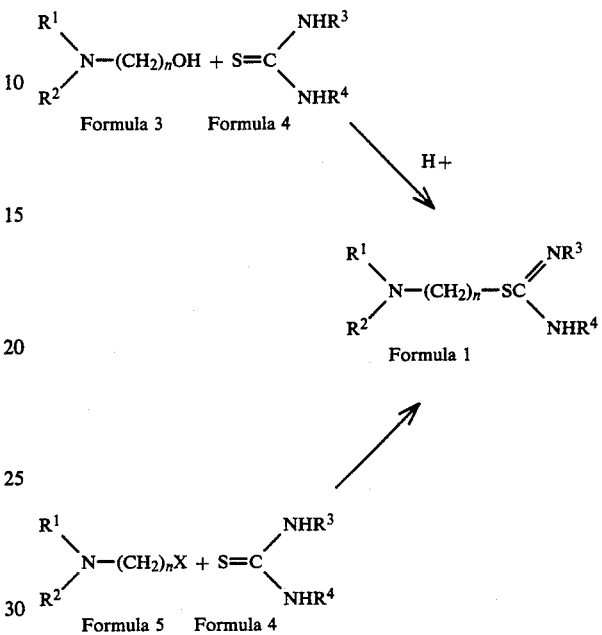

A dialkylaminoalkanol of Formula 3 and a thiourea of Formula 4, wherein $R^3$ and $R^4$ are as defined in Formula 1, are heated together under suitable acidic conditions, e.g., refluxed in 48% hydrobromic acid, to give a compound of Formula 1.

Alternatively, a dialkylaminoalkyl halide of Formula 5 wherein X is halogen for example chlorine and a thiourea of Formula 4 are heated together to give a compound of Formula 1. Preferably, this reaction is carried out using a lower alkanol as a solvent at an elevated temperature e.g., 100°–150° C.

The compounds and pharmaceutical compositions of this invention have immunosuppressant activity, that is they delay the onset and/or decrease the magnitude of immunological reactions. Thus the compounds and compositions of this invention are valuable in the treatment of conditions where immunological reactions cause undesirable effects. For example the immunological reactions which cause graft rejection in warm-blooded animals may be reduced or delayed by administration of the compounds and compositions of this invention. The compounds and compositions of this invention are also useful in suppressing delayed hypersensitivity reactions, such as contact sensitivity to metal ions, and in suppressing autoimmune diseases, such as rheumatoid arthritis and psoriasis.

The immunosuppressant activity of the compounds of Formula 1 may be demonstrated by the following tests:

(1) Inhibition of mitogen-induced lymphocyte transformations. The compounds of this invention inhibit the transformation of human blood T-lymphocytes into blast cells induced by phytohaemagglutinin (mitogen). The compounds of Formula 1 show significant activity in this test at concentrations of $10^{-5}M$.

(2) Inhibition of allograft rejection. The compounds of Formula 1 delay the rejection of C3H skin grafts on C57BL mice as measured using the pinch graft technique of Billingham and Medawar (J. Exp. Biol. 28, 385 (1951)) at dose levels about 200 μm/kg. s.c.

(3) Inhibition of delayed hypersensitivity reactions. The compounds of Formula 1(a) inhibit a delayed tuberculin-type reaction to ovalbumin in guinea pigs and (b) inhibit a contact sensitivity reaction to oxazolone in mice. The compounds of Formula 1 showed significant activity in these tests at dose levels about 200 μm/kg. s.c.

(4) Inhibition of antibody production. The compounds of Formula 1 inhibited the production of IgM antibodies the sheep erythrocytes in mice (measured by a modified Jerne plaque assay described in Wortis et al. Immunology 17, 93, (1969) at dose levels about 50 μm/kg. s.c.

In addition, the compounds of this invention show acute anti-inflammatory activity in conventional tests such as the rat paw oedema or the guinea-pig U.V. erythema tests. In the former the oedema is induced by an irritant, and in the latter the depilated skin of the guinea-pig is exposed to U.V. radiation and an erythema results. Subcutaneous injection of doses of about 0.5 mmol/kg of a compound of Formula 1 reduces the rat paw volume in the former test and reduces the intensity of the guinea-pig erythema in the latter test.

A useful modification of the guinea-pig U.V. erythema test is to irradiate only the whole ear and measure the ear temperature by a thermistor probe. Subcutaneous injection of doses of about 0.2 mmol/kg of a compound of Formula 1 to a guinea-pig reduces the rise in ear temperature caused by U.V. irradiation.

Activity in this animal test is indicative that the compounds will be useful in treating inflammatory conditions such as arthritis in humans.

The nature of the pharmaceutical composition will of course depend on the nature of the condition being treated and the intended route of administration i.e., topical, oral or parenteral. Advantageously the composition will be made up in a dosage unit form appropriate to the desired mode of administration, for example as a tablet, capsule, ointment, cream or injectable solution.

Other pharmacologically active compounds may in certain cases be included in the composition.

For therapeutic use, the pharmacologically active compounds of Formula 1 will normally be administered as a pharmaceutical composition comprising as the or an essential active ingredient, at least one such compound in the basic form or in the form of an addition salt with a pharmaceutically acceptable acid and in association with a pharmaceutical carrier therefor. Such addition salts include those with hydrochloric, hydrobromic hydriodic, sulphuric and maleic acids and may conveniently be formed from the compounds of Formula 1 by standard procedures for example by the use of ion exchange resins to form the required salt from a different addition salt.

The pharmaceutical carrier employed may be, for example, either a solid or liquid. Exemplary of solid carriers are lactose, maize or potato or modified starches, dicalcium phosphate, terra alba, sucrose, celluloses, talc, gelatin, microfine silica, agar, pectin, acacia, magnesium stearate, stearic acid and the like. Exemplary of liquid carriers are syrup, peanut oil, olive oil, alcohol, propylene glycol, polyethylene glycols, water and the like.

A wide variety of pharmaceutical forms can be employed. Thus, if a solid carrier is used, the preparation can be tableted, placed in a hard gelatin capsule in powder or pellet form, or prepared in the form of a troche or lozenge. The amount of solid carrier will vary widely but preferably will be from about 25 mg to about 1 g. If a liquid carrier is used, the preparation may be in the form of a syrup, emulsion, multiple emulsion, sterile injectable liquid or an aqueous or non-aqueous solution or liquid suspension. Other additives such as preservatives e.g., antioxidants or antibacterials and/or flavouring or colouring agents may also be included. The liquid forms may also be prepared in soft gelatin capsules or microcapsules. The sterile solution may be prepared in ampoules, multidose vials or unit dose disposable syringes. The preparation may also be in a semi-solid form such as a cream, paste, ointment or gel or a liquid or aerosol form for topical administration.

The pharmaceutical compositions are prepared by conventional techniques, involving procedures such as milling, mixing, granulating and compressing, spray drying, freeze drying or dissolving or dispersing the ingredients as appropriate to the desired preparation.

The active ingredient will be present in the compositions in the effective amount to produce immunosuppressant activity. The route of administration may be topical, oral or parenteral.

The dose regime will depend on the condition being treated, the route of administration, and the particular pharmaceutical formulation chosen. Generally, the unit dose will contain from about 25 mg to about 700 mg of a compound of Formula 1, and preferably from about 200 to about 500 mg of a compound of Formula 1.

The method of producing antiinflammatory activity by administering the compounds of Formula 1 is also an object of this invention. The compound of Formula 1 is administered in an amount sufficient to produce antiinflammatory activity. The daily dosage will preferably be from about 25 mg. to about 1 g.

The invention is illustrated by the following examples wherein all temperatures are in degrees Centigrade:

EXAMPLE 1

2-(3-Dimethylaminopropylthio)-2-imidazoline

A mixture of N,N$^1$-ethylenethiourea (10.2 g), 3-dimethylaminopropyl chloride hydrochloride (15.8 g) and ethanol (30 ml) was heated under reflux in an oil bath at 140°–145° for 24 hours. The ethanol was removed by evaporation and the solid residue was recrystallised from ethanol to give 2-(3-dimethylaminopropylthio)-2-imidazoline dihydrochloride (19.6 g) m.p. 180°. A second recrystallisation from ethanol gave a sample with m.p. 177°–178.5°.

(Found: C, 36.6; H, 7.3; Cl, 27.4; N, 16.0; S, 12.2; $C_8H_{17}N_3S.2HCl$, requires: C, 36.9; H, 7.4; Cl, 27.25; N, 16.15; S, 12.3%.

EXAMPLE 2

2-(2-Dimethylaminoethylthio)-2-imidazoline

A mixture of N,N$^1$-ethylenethiourea (10.2 g), 2-dimethylaminoethyl chloride hydrochloride (14.4 g) and ethanol (30 ml) was heated under reflux in an oil-bath at 140°–144° for 24 hours and allowed to cool. The solid which crystallised out was recrystallised once from 90% ethanol and twice from 80% isopropanol to give the dihydrochloride of the title product (19 g) m.p. 192°–193°.

EXAMPLE 3

N,N¹-Dimethyl-S-(3-dimethylaminopropyl)isothiourea

A mixture of 3-dimethylaminopropanol (10.3 g), N,N¹-dimethylthiourea (10.4 g) and aqueous hydrobromic acid (48%, 60 ml) was boiled under reflux for 18 hours and evaporated to dryness. The residue was recrystallised from ethanol to give the dihydrobromide of the title compound m.p. 173°–174°.

(Found: C, 27.4; H, 6.0; N, 12.0; S, 9.1; Br, 45.3; $C_8H_{19}N_3S.2HBr$, requires: C, 27.4; H, 6.0; N, 12.0; S, 9.1; Br. 45.5%.

EXAMPLE 4

N,N¹-Dimethyl-S-(2-dimethylaminoethyl)isothiourea

A mixture of 2-dimethylaminoethanol (2.23 g), N,N¹-dimethylthiourea (2.6 g) and aqueous hybrobromic acid (48%, 20 ml) was boiled under reflux for 50 hours and evaporated to dryness. The residue was recrystallised from a mixture of methanol and ethanol to give the dihydrobromide of the title compound (5.6 g) m.p. 198°–199°.

(Found: C, 24.9; H, 5.7; N, 12.7; S, 9.5; Br, 47.2; $C_7H_{17}N_3S.2HBr$ requires: C, 24.9; H, 5.7; N, 12.5; S, 9.5; Br, 47.4%)

EXAMPLE 5

N,N¹-Dibutyl-S-(3-dimethylaminopropyl)isothiourea

When, N,N'-dibutylthiourea is substituted for N,N'-dimethylthiourea in the procedure of Example 3, the dihydrobromide salt of the title compound is prepared.

EXAMPLE 6

N,N'-Dimethyl-S-(3-dibutylaminopropyl)isothiourea

When 3-dibutylaminopropanol is substituted for 3-dimethylaminopropanol in the procedure of Example 3 the dihydrobromide salt of the title compound is prepared.

EXAMPLE 7

N-Ethyl-N'-methyl-S-(3-ethylaminopropyl)isothiourea

A mixture of 3-(ethylmethylamino)propanol, N-ethyl-N'-methylthiourea and aqueous hydrobromic acid is boiled under reflux to give the dihydrobromide salt of the title compound.

EXAMPLE 8

2-[2-(4-morpholino)ethylthio]-2-imidazoline dihydrochloride

A mixture of freshly recrystallised N,N'-ethylene thiourea (10.2 g), N-(2-chloroethyl)-morpholine hydrochloride (18.6 g) and ethanol (100 ml) was boiled under reflux in an atmosphere of nitrogen for 3 days and allowed to cool. The solid which crystallised out was recrystallised twice from ethanol to give the title compound, (4.0 g) m.p. 235°–236° C.

(Found: C, 37.58; H, 6.52; Cl, 24.07; N, 14.63; S, 11.24%. $C_9H_{17}N_3OS.2HCl$, requires: C, 37.50; H, 6.64; Cl, 24.60; N, 14.58; S, 11.12%)

EXAMPLE 9

2-[2-(1-Piperidino)ethylthio]-2-imidazoline dihydrochloride

A mixture of N,N'-ethylene thiourea (10.2 g), N-(2-chloroethyl)piperidine hydrochloride (18.4 g) and ethanol (100 ml) was boiled under reflux in an atmosphere of nitrogen for 3 days and allowed to cool. The solid which crystallised out was recrystallised three times from ethanol to give impure product; the filtrates from the second and third crystallisations were combined and concentrated to afford the required product, which after one further crystallisation from ethanol yielded the title compound (3.1 g) m.p. 236°–237° C.

(Found: C, 41.83; H, 7.31; Cl, 24.46; N, 14.73; S, 11.27% $C_{10}H_{19}N_3S.2HCl$., requires: C, 41.96; H, 7.39; Cl, 24.77; N, 14.68; S, 11.20%).

EXAMPLE 10

2-[2-(1-Pyrrolidino)ethylthio]-2-imidazoline dihydrochloride

A mixture of N,N'-ethylenethiourea (10.2 g), N-(2-chloroethylpyrrolidine hydrochloride (17.0 g) and ethanol (100 ml) was boiled under reflux in an atmosphere of nitrogen for 3 days and allowed to cool. The solid which crystallised out was recrystallised from ethanol and then chromatographed on a column of silica gel using methanol for elution. The eluate was concentrated and the resulting solid was crystallised from ethanol, and then twice from isopropanol to yield the title compound (1.1 g) m.p. 211°–212° C.

(Found: C, 39.41; H, 6.97; Cl, 25.65; N, 15.06; S, 11.63% $C_9H_{17}N_3S.2HCl$., requires: C, 39.71; H, 7.03; Cl, 26.05; N, 15.44; S, 11.78%)

EXAMPLE 11

2-(4-Dimethylaminobutylthio)-2-imidazoline

When 4-dimethylaminobutyl chloride is substituted for 3-dimethylaminopropyl chloride in the procedure of Example 1 the dihydrochloride of the title compound is produced.

EXAMPLE 12

When in the procedure of Example 1 1-(2-chloroethyl)-4-methylpiperazine or 1-(2-chloroethyl)-(1H)-hexahydroazepine are substituted for 3-dimethylaminopropyl chloride the products are, respectively:

2-[2-(4-methyl-1-piperazino)ethylthio]-2-imidazoline dihydrochloride and

2-[2-(1-(1H)-hexahydroazepino)ethylthio]-2-imidazoline dihydrochloride.

EXAMPLE 13

When in the procedure of Example 2, 2-(1H)-tetrahydropyrimidinethione or hexahydro-(2H)-1,3-diazepine-2-thione is reacted with 2-dimethylaminoethyl chloride hydrochloride the products are respectively:

2-(2-dimethylaminoethylthio)-2-tetrahydropyrimidine dihydrochloride and 2-(2-dimethylaminoethylthio)-2-hexahydro-1,3-diazepine dihydrochloride

EXAMPLE 14

| Tablet Formulation | |
|---|---|
| Ingredient | mg/tablet |
| 2-(2-Dimethylaminoethylthio)-2-imidazoline dihydrochloride | 250.0 |
| Avicel PH 101 (microcrystalline cellulose) | 50.0 |
| Polyvinylpyrrolidone | 10.0 |
| Sodium Lauryl Sulphate | 0.5 |
| Primojel (sodium starch glycollate) | 15.0 |
| Magnesium Stearate | 1.0 |

-continued

| Tablet Formulation | |
|---|---|
| Ingredient | mg/tablet |
| Maize Starch | 15.0 |

2-(2-Dimethylaminoethylthio)-2-imidazoline dihydrochloride and Avicel are passed through a 40 mesh screen and mixed until homogeneous. The polyvinylpyrrolidone and sodium lauryl sulphate are dissolved in water and this solution is added, with mixing to the drug/Avicel mixture, and water is added until the correct consistency for granulation is achieved. The resultant mixture is passed through a 14 mesh screen to give granules which are dried and passed through a 60 mesh screen and added to the granules. This composition is mixed until homogeneous and tableted.

EXAMPLE 15

| | Cream Formulation | |
|---|---|---|
| A | Stearyl Alcohol | 15.0% |
| | Beeswax | 8.0% |
| | Arlacel 80 (sorbitan mono-oleate) | 1.25% |
| | Tween 80 (polyoxyethylene sorbitan mono-oleate) | 3.75% |
| | 2-(2-Dimethylaminoethylthio)-2-imidazoline dihydrochloride | 1.0 |
| B | Sorbitol Solution B.P. | 7.5% |
| | Citric Acid | 0.2% |
| | Sodium citrate | 0.05% |
| | Methylparaben | 0.18% |
| | Propylparaben | 0.02% |
| | Water to | 100.0% |

Mixture B is heated to 72° C. and added with agitation to mixture A at 70° C. The agitation is continued until a cream has formed.

EXAMPLE 16

By dissolving 300 mg of 2-(2-dimethylaminoethylthio)-2-imidazoline dihydrochloride in 2 ml of buffered saline solution a pharmaceutical composition suitable for parenteral administration is prepared.

The pharmaceutical compositions prepared as in the foregoing examples are administered to a subject in need thereof within the dose ranges given hereabove to produce immunosuppressant activity.

What we claim is:

1. A pharmaceutical composition having immunosuppressant activity comprising a pharmaceutical carrier and, in an effective amount to produce immunosuppressant activity, an isothiourea derivative of the formula:

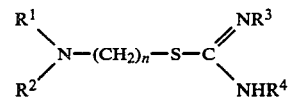

wherein n is 2, 3, or 4; $R^1$ and $R^2$ together with the nitrogen atom shown form a morpholine ring; and $R^3$ and $R^4$, which may be the same or different, are lower alkyl, or together may form a —$(CH_2)_x$— group where x is 2, or a pharmaceutically acceptable acid addition salt thereof.

2. A pharmaceutical composition according to claim 1 wherein n is 2 and $R^3$ and $R^4$ are lower alkyl.

3. A pharmaceutical composition according to claim 1 wherein n is 2 or 3 and $R^3$ and $R^4$ together with the two nitrogen atoms and the carbon atoms shown form an imidazoline ring.

4. An isothiourea derivative of the formula:

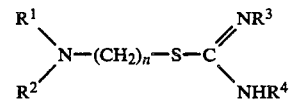

wherein n is 2, 3, or 4; $R^1$ and $R^2$ together with the nitrogen atom shown form a morpholine ring; and $R^3$ and $R^4$, which may be the same or different, are lower alkyl, or together may form a —$(CH_2)_x$—group wherein x is 2; or a pharmaceutically acceptable acid addition salt thereof.

5. An isothiourea according to claim 4 wherein n is 2 or 3.

6. An isothiourea according to claim 4 wherein n is 3 and $R^3$ and $R^4$ are lower alkyl or together with the two nitrogen atoms and the carbon atom shown form an imidazoline ring.

7. An isothiourea according to claim 4 wherein $R^3$ and $R^4$ together with the two nitrogen atoms and the carbon atom shown form an imidazoline ring.

* * * * *